United States Patent [19]

Hasenbeck

[11] 4,137,931
[45] Feb. 6, 1979

[54] CONDUCTION TYPE SOIL MATRIC POTENTIAL SENSOR

[76] Inventor: Harold W. Hasenbeck, 1524 Alameda St., Pomona, Calif. 91767

[21] Appl. No.: 759,782

[22] Filed: Jan. 17, 1977

[51] Int. Cl.² ............................................. A01G 25/00
[52] U.S. Cl. ......................................... 137/78; 73/73; 324/65 R; 324/65 P; 338/34
[58] Field of Search ................ 137/78; 73/73; 239/63, 239/64; 338/34, 35; 324/65 P

[56] References Cited

U.S. PATENT DOCUMENTS

| 2,941,174 | 6/1960 | Richards | 73/73 X |
| 3,206,615 | 9/1965 | La Pointe | 340/244 C |
| 3,847,351 | 11/1974 | Hasenbeck | 239/63 |

OTHER PUBLICATIONS

Popular Electronics, vol. 1, No. 1, Jan. 1972, Ziff–Davis Publ. Co., N.Y., N.Y., p. 102.

Primary Examiner—Alan Cohan
Assistant Examiner—Richard Gerard
Attorney, Agent, or Firm—William W. Haefliger

[57] ABSTRACT

A matric potential sensor comprises
(a) a housing including a porous wall adapted to be located underground,
(b) spaced electrodes carried in the housing to be coupled to a source of electrical current, and
(c) granular material located to pass electrical current within the housing and between the electrodes so that the current flow will vary as a function of the moisture content of the granular material, said content adapted to vary as a function of the matric potential of the soil surrounding the housing in response to moisture transmission through the porous housing into the surrounding soil.

Special circuitry adapts the sensor for use with a solenoid type irrigation valve controller.

6 Claims, 7 Drawing Figures

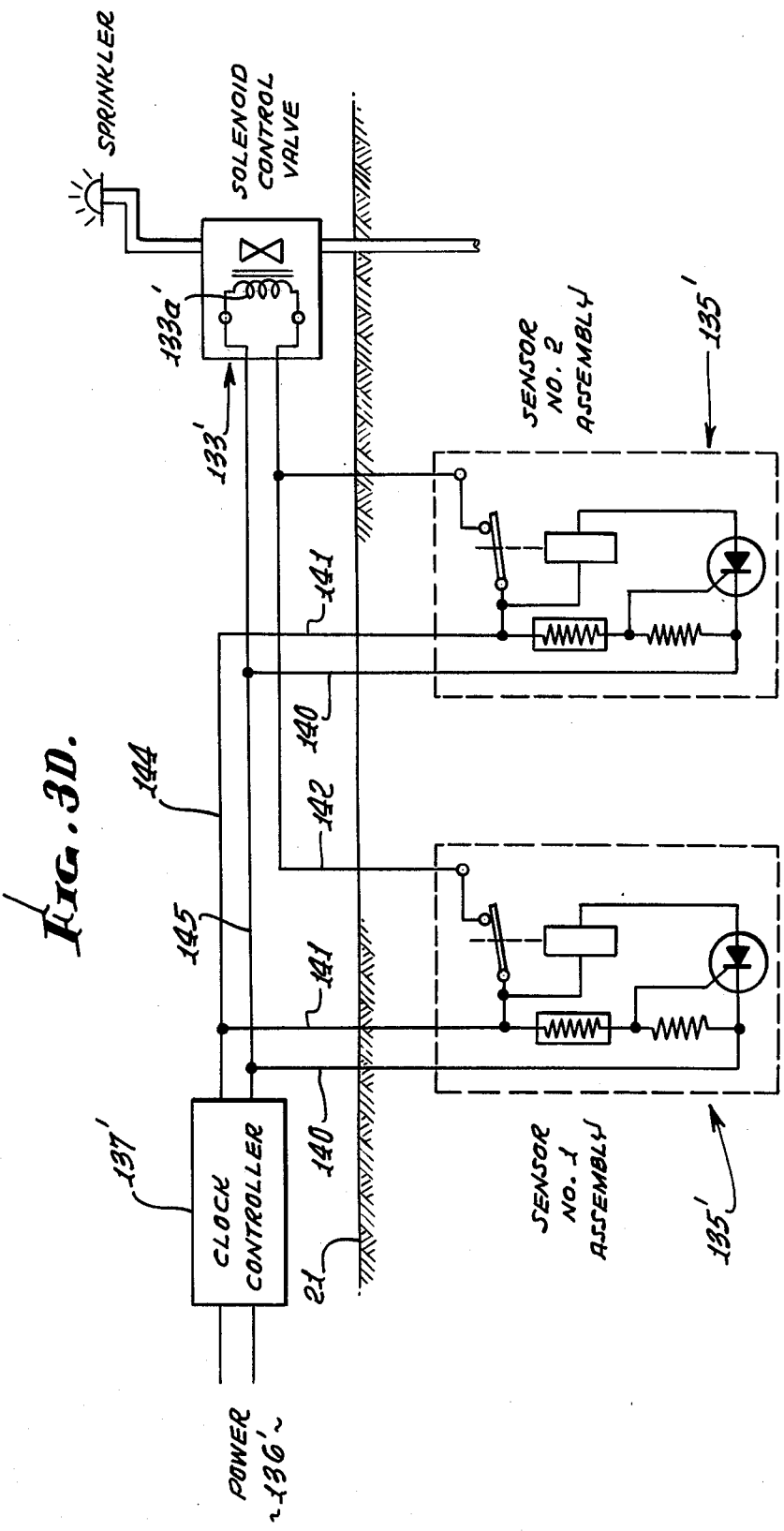

CONDUCTION TYPE SOIL MATRIC POTENTIAL SENSOR

BACKGROUND OF THE INVENTION

This invention relates generally to irrigation control systems, and more particularly concerns an improved sensor that is matric potential responsive.

Plant root systems extract moisture from the soil continuously during their lifetime. As water is depleted in the soil adjacent to the root system, voids appear in between the soil particles. Since adjacent undepleted moist soil forms a tight seal, the voids thus formed in the water depleted area create a vacuum or suction, the degree of which depends upon the amount of water removed by the root systems. As the partial vacuum increases, it becomes increasingly difficult for the plant roots to extract the required moisture and transport it to the plant structure. This increased vacuum or suction is known as moisture tension and, in recent soil science terminology, is known as matric potential.

It has been determined that most plant growth and crop yield decreases as a function of the stress resulting from matric potential, the maximum yield occuring at matric potential values between $-10$ to $-50$ centibars suction. However, because of the wide differences in the grain size and mix of various soils, e.g. fine sand versus clay, the amount of soil moisture which can be removed by the root system, for a given low matric potential, is quite large; i.e., in fine sand, roots can extract all but a few percent of the contained moisture without exceeding $-50$ centibar suction. At the other end of the soil scale, the millimicron particles of clay have such a high capillary attraction for water the matric potential may reach $-50$ centibar suction even though the moisture in the clay is as high as 40%.

The wide difference in soil moisture content, as a function of plant root stress, is of great importance to proper design of sensors for controlling irrigation systems. Unless a soil sensor is responsive to changes in matric potential, each soil type would require a separate sensor calibration; e.g. 7% soil moisture in fine sand having $-50$ centibar suction, 40% soil moisture in clay having $-50$ centibar suction. For this situation, sensors measuring resistance change as a function of soil moisture would require a 6 to 1 difference in their calibration in order to control irrigation at $-50$ centibar suction. The same holds true for heat-diffusion sensors (as described in U.S. Pat. No. 2,718,141, L. C. Richards 1955), U.S. Pat. Nos. 2,343,520 & 2,362,344, Baver (1944), since the heat transfer is a direct function of the soil moisture content.

SUMMARY OF THE INVENTION

It is a major object of the present invention to provide a simple matric potential sensor connectible to a power source, and wherein current through porous material located between metal plates will vary as a function of moisture content of the porous material, i.e., the current will be high when the moisture content is high, and low when the moisture content is low.

Basically, the improved sensor comprises (a) a housing including a porous wall adapted to be located underground, (b) spaced electrodes carried by the housing to be coupled to a source of electrical current, and (c) porous granular material located to pass electrical current within the housing and between the electrodes so that the current flow will vary as a function of the moisture content of the granular material, said content adapted to deplete its moisture when the soil surrounding the housing reaches a predetermined range of soil matric potential, As will be seen, the electrodes, such as plates are typically carried by the housing to provide relatively high current flow when the soil matric potential is low, and extremely low current when a pre-selected soil matric potential prevails.

A second object of the invention is to provide an irrigation control system wherein a second and like sensor is located in communication with an irrigation water supply line. As will be seen, an electrical current is connected in common with the two sensors (one underground in the soil to be irrigated, and the other in the irrigation water supply line) to provide a comparison of the electrical impedances of the two sensors, whereby the supply of irrigation water may be controlled as a consequence of the comparison. As a result, the system is sensitive to salt build-up in the soil electrolyte at the sensor location.

A third application of the sensor is realized if all of the irrigation control elements are assembled in close proximity to, and become an integrated part of, the sensor assembly. This arrangement allows power to be switched to the sensor at any convenient time; e.g. switched ON by a clock controller. However, if the sensor does not command irrigation, power is not switched to the valve for irrigation.

These and other objects and advantages of the invention, as well as the details of an illustrative embodiment, will be more fully understood from the following drawings and detailed description, wherein:

DRAWING DESCRIPTION

FIGS. 3A, 3B, 3C and 3D are circuit diagrams showing advantageous modes of use of the sensor.

DETAILED DESCRIPTION

Figure 1:
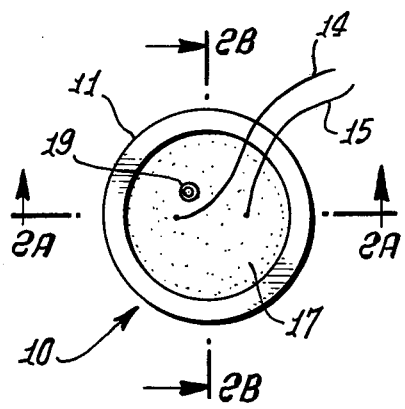
FIG. 1 is a top plan view of one form of sensor embodying the invention.
Figure 2A:
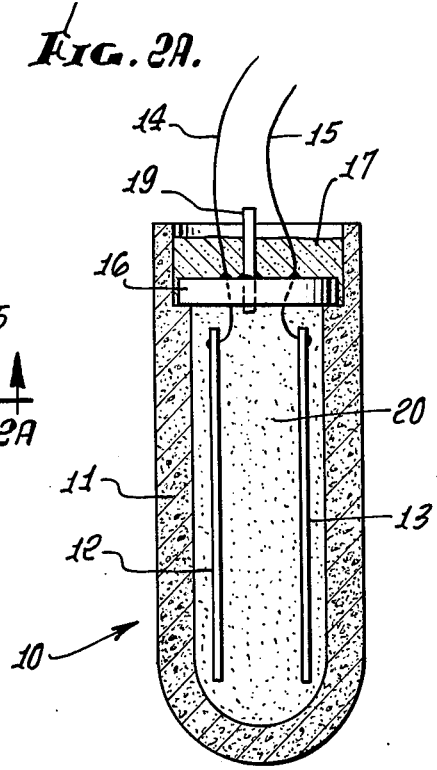
FIGS. 2A and 2B are vertical sections through the FIG. 1 sensor and taken on lines 2A—2A and 2B—2B, respectively.
Figure 2B:
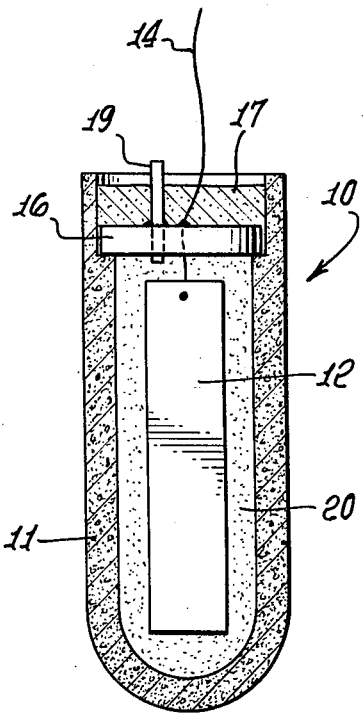

Referring first to FIGS. 1 and 2, the illustrated matric potential sensor 10 comprises a housing or container including a porous wall 11 adapted to be located underground, and spaced electrodes, such as metal plates carried by the housing to be coupled to a source of electrical current. Electrical conductors 14 and 15 are connected with the plates 12 and 13 which are metallic and spaced apart. Usable material for the porous housing includes polyethylene, ceramic, gypsum, or any inert material whose pore size is less than the pore size of the material contained. The housing may be cylindrical as shown, and the rectangular, electrically conductive elongated plates may be received into the elongated housing as shown. A holding cap 16 is retained in place by sealant 17. A vent tube 19 is provided through the cap 16 and sealant 17.

Granular material 20 is packed in the housing and located to pass electrical current within the housing and between the plates so that current flow will vary as a function of the moisture content of the material. Such moisture content decreases greatly when the matric potential of the surrounding soil 21 reaches a predetermined bubbling pressure of the sensor granular material, thereby initiating rapid moisture transmission from the housing 11, into the surrounding soil. In this regard, plates 12 and 13 are typically carried in the housing to provide relatively high current flow when the moisture content of the material 20 is relatively high, and to produce low current flow when the moisture content of the material 20 is low.

A unique feature, and the one which lends itself to accurate irrigation control, is the large reduction in cell current when the matric potential of the soil reaches the bubbling pressure point with regard to the withdrawal of water from a given type of contained granular material. This arrangement, when placed in soil with approximately zero matric potential, (water saturated), provides an initial resistance between the sensor plates of the order of 200 ohms. However, when the matric potential increases to a level which matches the bubbling pressure of the granular material between the plates of the sensor, e.g. −24 centibars, the moisture between the sensor plates drops to a level which increases the resistance to a value of the order of 30,000 ohms or more than 150 times the initial zero matric potential value. This point of both rapid and high value change in circuit electrical current, provides an accurate means for controlling a current relay or sensing switching device designed to switch power 'ON' to an irrigation valve when the sensor circuit current reduces to some predetermined matric potential value.

SENSOR USED AS SALINITY DETECTOR

The sensor has another attribute which is of extreme importance for the prevention of crop damage by the build up of salt within the soil. Soil scientists have determined that salt in irrigation water crystalizes on the surface or in boundaries of the soil which become dry prior to rains or between irrigation intervals. Upon rewetting, the salt dissolves and some is carried by the water to the plant root zone. This process is repeated over a period of time until a point is reached where the salt content is so high plants find it toxic or the osmotic potential so high plant growth is greatly reduced. This is called Osmotic Potential stress. Normal practice requires an excess of irrigation water be used to flush or leach the soil until the salt is drained below or beyond the plant root system. The problem is knowing when salt leaching is required, and how much water is required to leach properly without waste.

The conduction cell type sensor can be arranged to make the determination automatically, since salt buildup in the soil electrolyte at the sensor location gradually reduces the sensor resistance. If a similar sensor is placed in the irrigation water supply line, the sensor control circuit can be arranged to compare the soil sensor with the water supply sensor and automatically start leaching when the resistance of the soil sensor is some predetermined amount lower than the supply water sensor. The circuit can be arranged to provide for continuous or intermittent irrigation until the soil sensor resistance increases to the point of leach turn-off.

DESCRIPTION OF CONTROL CIRCUIT

Figure 3A:
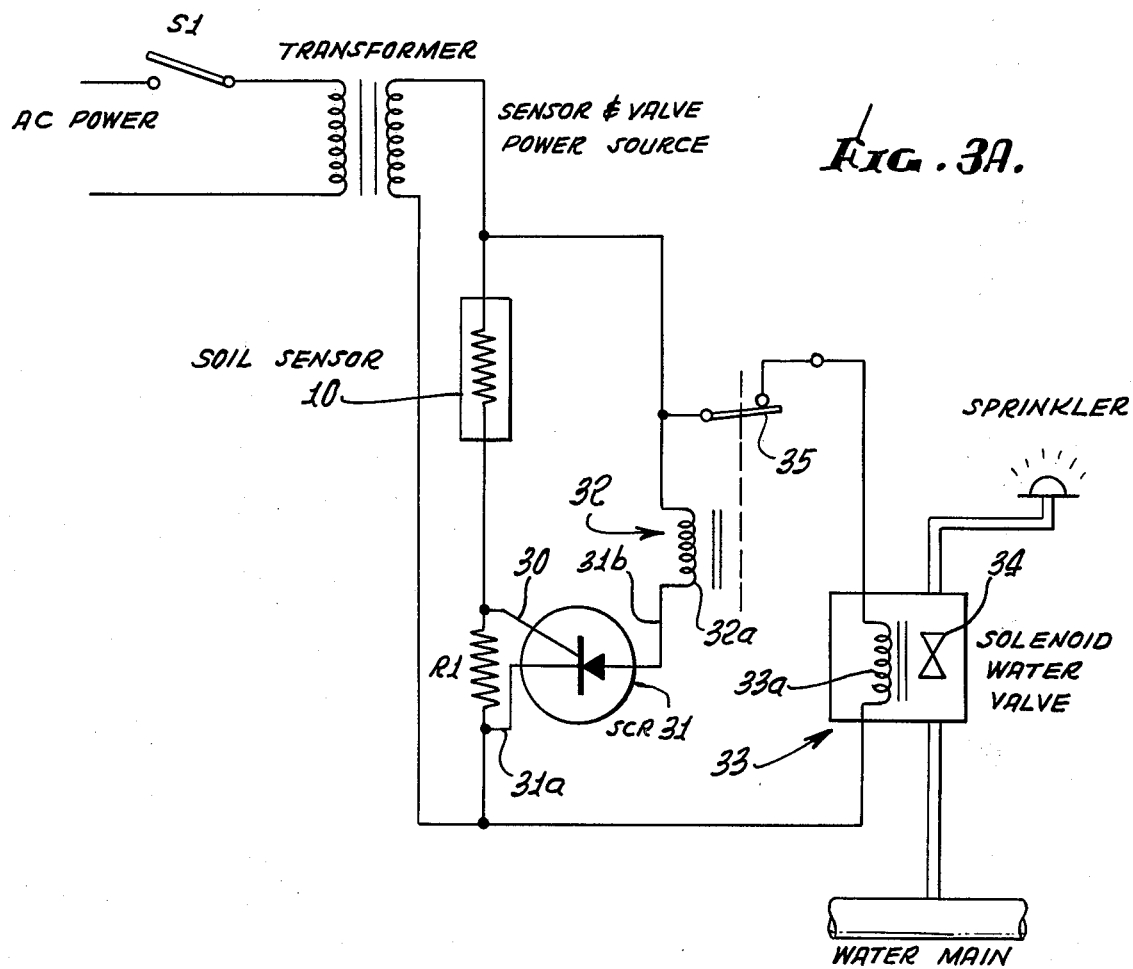

In the FIG. 3A circuit, when $S_1$ closes, current flows through the soil sensor 10 and $R_1$. The amount of current is determined by the amount of moisture in the soil sensor. High water content produces high current and low content produces low current. Resistance $R_1$ is selected to maintain the gate 30 of the semiconductor, such as the illustrated SCR 31 at a voltage that keeps the SCR conducting when the sensor is wet, thus actuating the relay 32. When the relay is actuated, the water valve electrical circuit is open and irrigation is off, i.e., switch arm 35 is open, no current flows to the coil 33a of solenoid 33, and water valve 34 is closed.

When the soil surrounding the Soil Sensor 10 reaches a predetermined matric potential value, water is withdrawn from the sensor and its resistance increases. The current through $R_1$ decreases until a point is reached at which the voltage across $R_1$ is too low to keep the SCR conducting. This deactivates the relay, closing the relay contacts which supplies power to the electric water valve 33 to start irrigation. Irrigation will continue until the matric potential of the soil around the soil sensor reduces to a range below the preset control point of the sensor. Note the SCR terminals 31a and 31b connected to the lower end of $R_1$ and to the relay coil 32a.

Figure 3B:
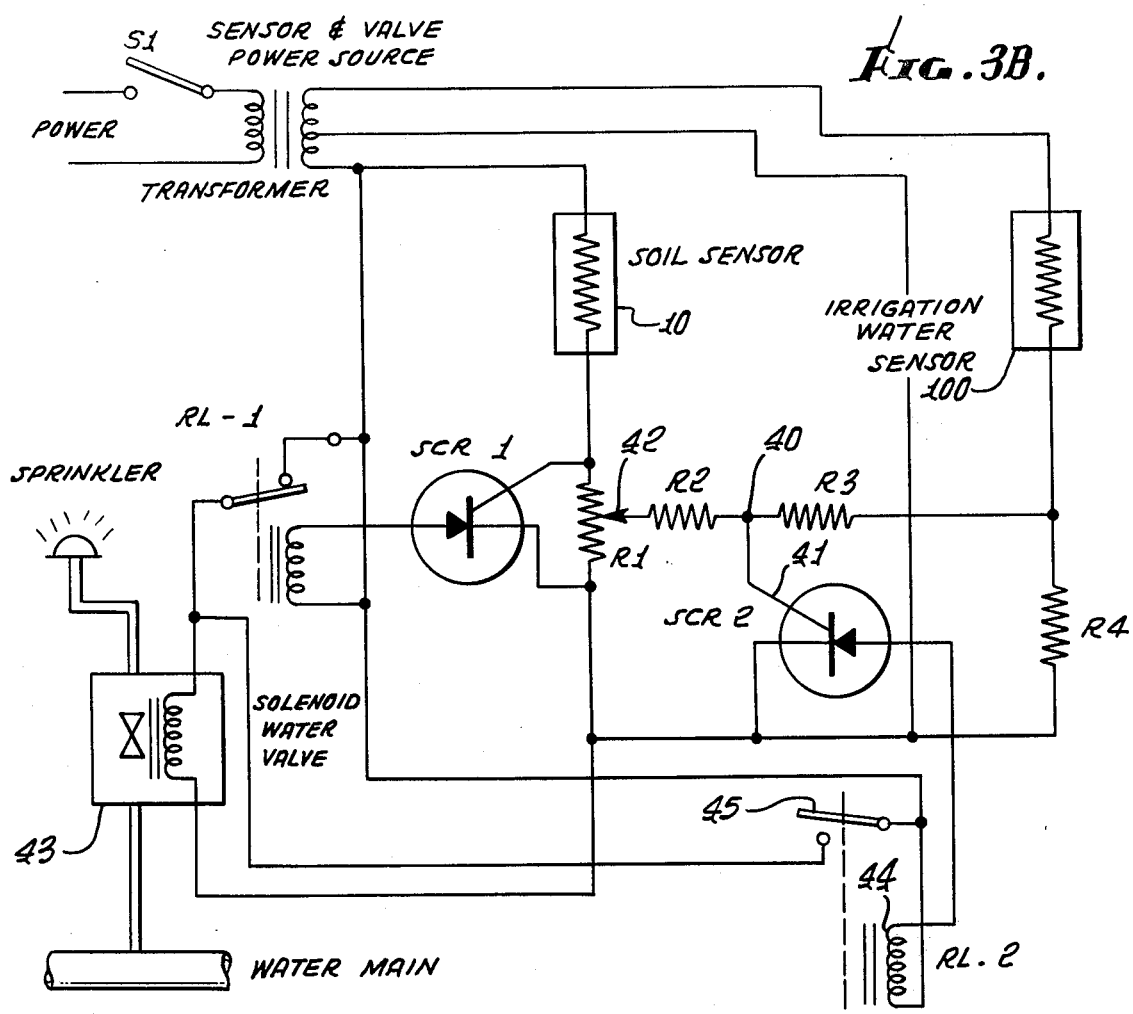

The circuit shown in FIG. 3B provides both automatic irrigation, commanded by the soil sensor 10 when the root stress reaches a predetermined matric potential, and automatic leaching when the soil sensor resistance decreases a predetermined amount due to salt buildup in the soil. This change, compared to the resistance of irrigation water sensor 100 is measured in terms of voltage at the junction 40 of voltage divider $R_2$, $R_3$ which connects to the gate terminal 41 of $SCR_2$. $R_2$ also connects to $R_1$ at adjustable wiper 42. When the gate voltage turns $SCR_2$ ON, current flows through coil 44 of relay 2 which actuates arm 45 and switches the irrigate valve 43 ON. Leaching will continue until the salt is driven out of the soil sensor. When balance occurs, the voltage at the junction 40 of $R_2$, $R_3$ decreases and switches $SCR_2$ OFF. This turns relay 2 off and stops leaching.

The degree of salt buildup in the soil prior to leaching can be set by adjusting the arm position of wiper 42. Decreasing the resistance between wiper 42 and point A requires a higher salt buildup to initiate leaching.

Usable granular material 20 may include glass beads or other equivalently suitable material. Tests have proven that a volume of glass beads of a given diameter, e.g. 50 microns, provides a means of holding water until a given suction is reached (3.98 psi), at which time, a large percentage of water moves out of the volume of glass beads. The point at which this action takes place is known as the bubbling pressure. This bubbling pressure correlates directly to matric potential as a direct function of pressure to suction, the pressure being the bubbling pressure and the suction being the matric potential; equivalent only different in sign. By using glass beads of known uniform diameter, it is possible to fabricate a sensor with a very specific bubbling pressure. When placed in situ underground in equilibrium with the surrounding soil formation, the volume of glass beads will give up the greater part of its contained moisture when the surrounding soil reaches a particular matric potential. At this point, the binding tension of the water surrounding the beads is exceeded, and a large percentage of the water is removed from the bead volume. The removal of the water destroys the interlocking of the water film throughout the glass bead volume and to a large degree, destroys their ability to transmit electric current between their associated conducting plates. Some points at which various sphere diameters will give up moisture to soils at various matric potentials are as follows: 10 micron, −137 centibars, 75 microns −18 centibars, and 200 microns −6.8 centibars.

Figure 3C:
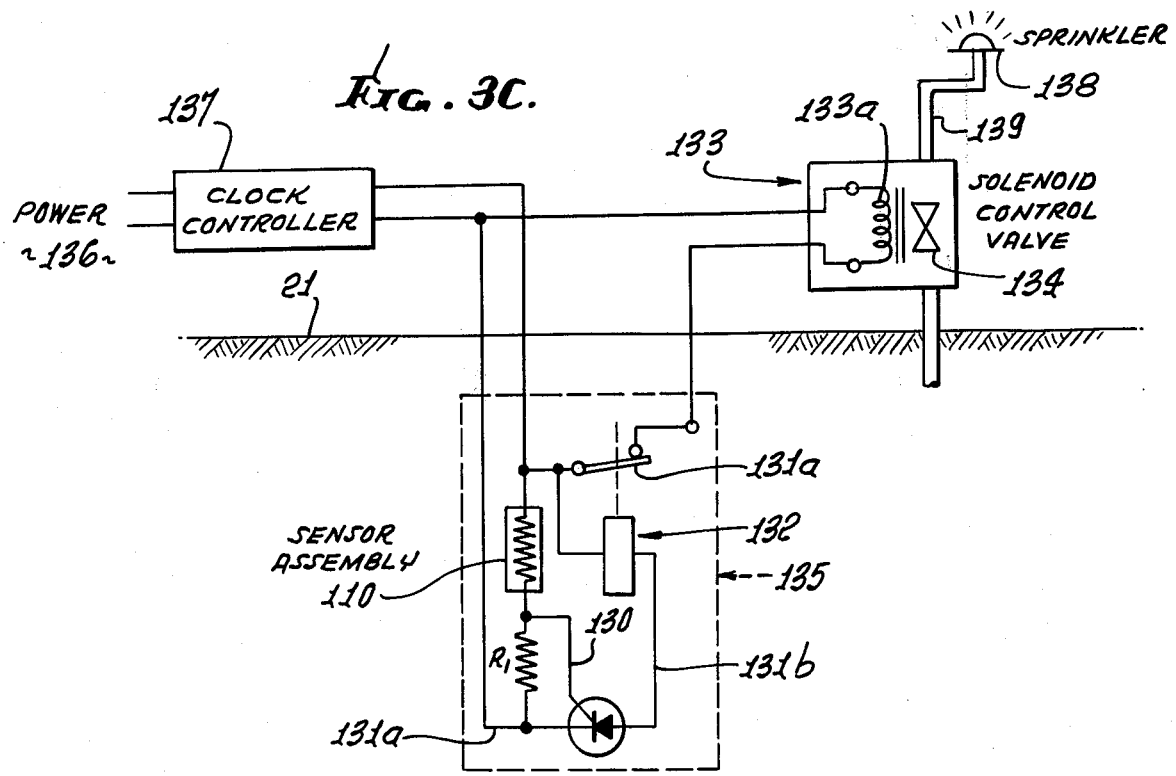

In FIG. 3c the elements are similar to those shown and described in FIG. 3A, and bear similar numbers except for a 1 before each number. All the irrigation control elements are assembled in close proximity to and become an integrated part of the sensor assembly. Note the broken line "box" 135 surrounding such elements, underground. Such a box might be encapsulated to seal the control components from moisture with the exception of the porous sensor 110 which must be in contact with the soil. This arrangement allows power (indicated at 136) to be switched to the sensor at any convenient time, i.e., switched ON by a timer or clock controller 137; however, if the sensor does not command irrigation, power is not switched to the valve 133 for irrigation. A sprinkler head 138 receives water from irrigation line 139 in which valve 133 is installed for flow control.

FIG. 3d shows an arrangement wherein two assemblies, as indicated at 135' (corresponding to assembly 135 in FIG. 3C), are each electrically connected in controlling relation with the solenoid control valve 133, i.e., in "parallel" relation, so that the valve is turned ON by either sensor assembly. Note leads 140 and 141 of each assembly connected across the power lines 144 and 145 and assembly leads 142 connected with power lead 145 via the coil 133a' of the controller 133.

I claim:

1. In a matric potential sensor, the combination comprising
   (a) a housing including a porous wall adapted to be located underground,
   (b) spaced electrodes in the form of elongated metallic plates carried in the housing to be coupled to a source of electrical current, and (c) a mass of granular material in the form of glass beads located to pass electrical current within the housing and between the electrodes so that the current flow will vary as a function of the moisture content of the granular material, said content adapted to vary as a function of the matric potential of the soil surrounding the housing in response to moisture transmission through the porous housing into the surrounding soil,
   (d) the electrodes being spaced apart, and the beads located in the current path between the spaced electrodes, the electrodes being elongated and substantially surrounded by said beads which are sized to release substantial moisture retained therebetween when the surrounding soil reaches a selected matric potential, thereby to effect a substantially sharp cut-off of electrical current flow between the plates at that matric potential.

2. The combination of claim 1 wherein the plates are carried by the housing to provide relatively high current flow when the moisture content of the material is relatively high, and to produce relatively low current flow when the moisture content of the material is relatively low.

3. The combination of claim 2 wherein the wall forms a shell, said electrodes located within the shell.

4. The combination of claim 1 including electrical conductors electrically connected with said electrodes.

5. The combination of claim 1 including a semi-conductor having two terminals and a gate, a resistor connected in series with an electrode of the sensor and a power source, one of said terminals and said gate connected across the resistor, and a relay having a coil connected in series between the other terminal of the semiconductor and the power source, the relay having a switch controlling current application to a solenoid for operating control valve in an irrigation line.

6. In a matric potential sensor the combination comprising
   (a) a porous wall adapted to be located underground, the wall extending about an interior zone,
   (b) spaced electrodes in the form of elongated metallic plates carried in said zone to be coupled to a source of electrical current, and
   (c) a mass of granular material characterized as hydrophilic and as bodies having beadlike form and located to pass electrical current within said zone and between the electrodes so that the current flow will vary as a function of the moisture content of the granular material, said content adapted to vary as a function of the matric potential of the soil surrounding said wall in response to moisture transmission through the porous wall into the surrounding soil, said granular bodies having substantially the same physical and electrical characteristics as glass beads, said bodies being of substantially uniform size,
   (d) the electrodes being spaced apart, and the material located in the current path between the spaced electrodes, the electrodes being elongated and substantially surrounded by said beadlike form material sized to release substantial retained moisture when the surrounding soil reaches a selected matric potential, thereby to effect a substantially sharp cut-off of electrical current flow between the plates at that matric potential.

* * * * *